(12) United States Patent
Swain

(10) Patent No.: US 7,208,070 B2
(45) Date of Patent: Apr. 24, 2007

(54) STENT MANUFACTURE

(75) Inventor: Brian Swain, Tamworth (GB)

(73) Assignee: Anopol Limited, Birmingham (GB)

( * ) Notice: Subject to any disclaimer, the term of this patent is extended or adjusted under 35 U.S.C. 154(b) by 410 days.

(21) Appl. No.: 10/456,401

(22) Filed: Jun. 6, 2003

(65) Prior Publication Data

US 2004/0267351 A1    Dec. 30, 2004

(30) Foreign Application Priority Data

Jun. 6, 2002   (GB) ................................. 0212909.6

(51) Int. Cl.
*B23H 3/04*       (2006.01)
(52) U.S. Cl. .............. 204/286.1; 204/288; 204/297.01; 204/297.06; 204/297.07; 204/297.08
(58) Field of Classification Search ............ 204/286.1, 204/288, 285, 287, 297.01, 297.06, 297.07, 204/297.08
See application file for complete search history.

(56) References Cited

U.S. PATENT DOCUMENTS

| | | | |
|---|---|---|---|
| 1,783,885 A | 12/1930 | Martin et al. ............... | 204/278 |
| 3,766,046 A | 10/1973 | Flint ........................... | 204/297 |
| 6,193,863 B1 | 2/2001 | Kobayashi ................ | 204/288.3 |
| 6,299,755 B1 * | 10/2001 | Richter ........................ | 205/651 |
| 6,610,194 B1 | 8/2003 | Guerin ........................ | 205/678 |

FOREIGN PATENT DOCUMENTS

| | | |
|---|---|---|
| EP | 0253004 | 1/1988 |
| EP | 0721020 | 7/1996 |
| EP | 1070772 | 1/2001 |
| FR | 1377075 | 10/1964 |
| FR | 2795433 | 12/2000 |
| GB | 1057148 | 2/1967 |
| GB | 2016048 | 9/1979 |
| SU | 1657545 | 6/1991 |
| SU | 1715887 | 2/1992 |
| WO | 9829025 | 7/1998 |
| WO | 0100906 | 1/2001 |
| WO | 0161080 | 8/2001 |

* cited by examiner

*Primary Examiner*—Bruce F. Bell
(74) *Attorney, Agent, or Firm*—Baker Botts LLP

(57) ABSTRACT

The present invention provides improvements in methods for the manufacture of stents. Specifically, the invention provides methods wherein stents are placed on jigs of various designs which facilitate manufacture, stents carried by the jigs are immersed in liquid baths which contain an electrolyte, the stents are urged into contact with their associated electrodes while current is applied to those electrodes, and wherein the positions of contact between the stents and their respective electrodes are altered during processing without removing the stents from the jig. The method is applicable for electropolishing and electro-plating.

6 Claims, 5 Drawing Sheets

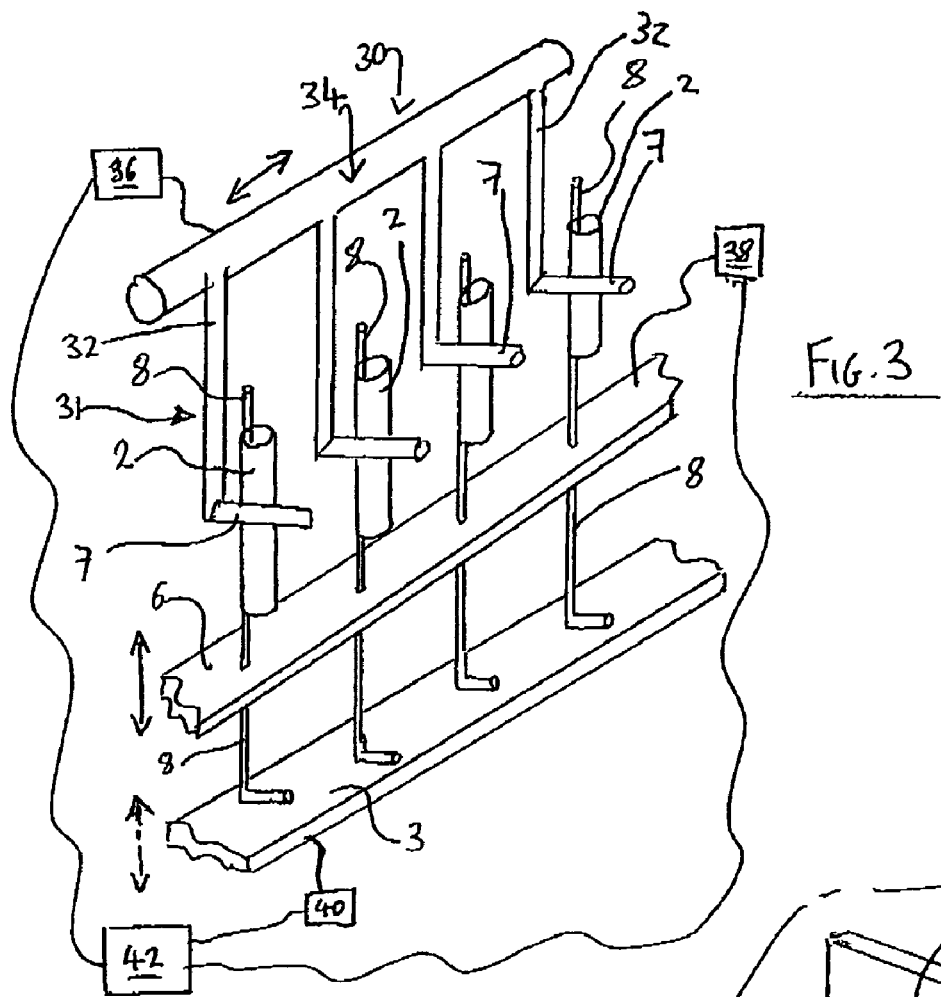
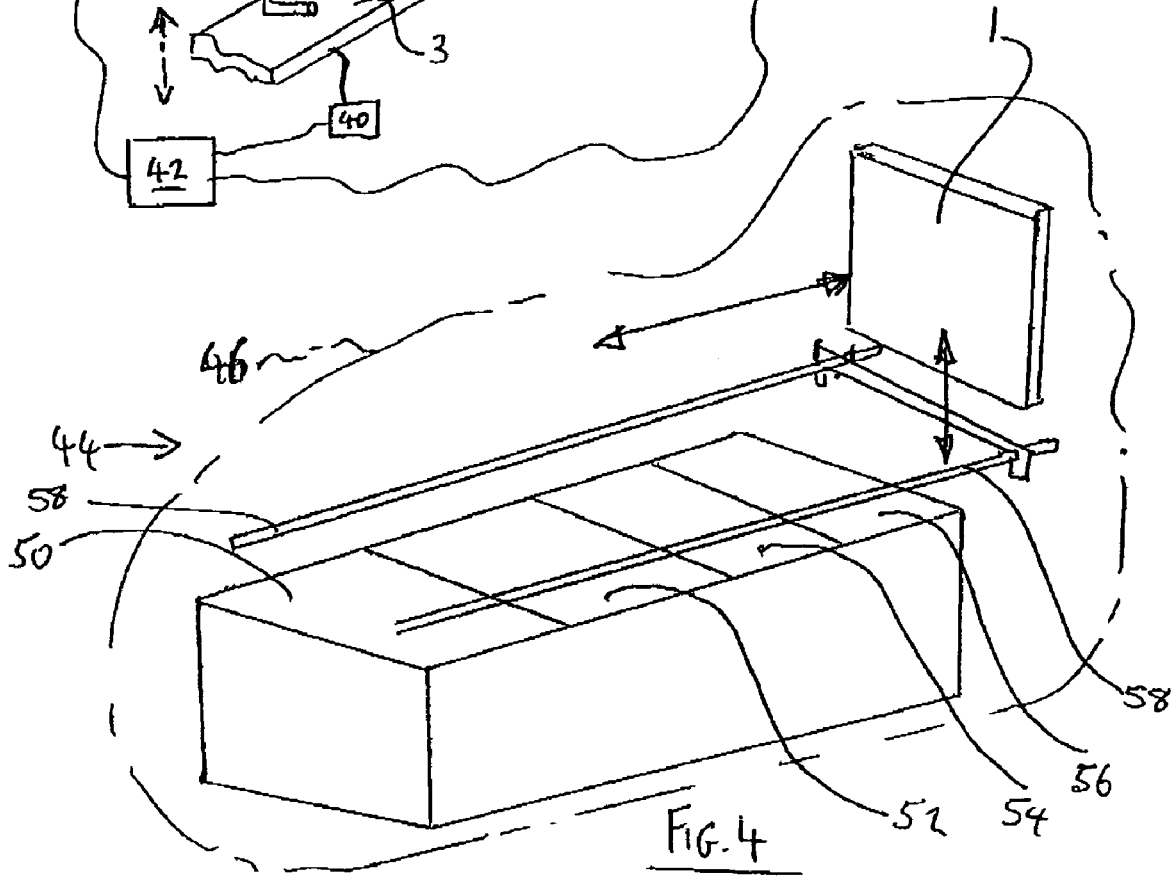

STENT MANUFACTURE

CROSS REFERENCE TO RELATED APPLICATIONS

This application claims priority under 35 U.S.C. § 119 to Great Britain Patent Application No. 0212909.6 filed Jun. 6, 2002, the contents of which are incorporated herein by reference.

BACKGROUND OF THE INVENTION

This invention relates to the manufacture of stents. The invention provides a new method of processing stents in at least one liquid bath, to a jig for supporting stents during such processing, processing equipment incorporating the new jig, and to stents so manufactured.

Stents used for implantation into veins or arteries are typically lattice-walled tubes which are extremely fragile. The basic manufacturing process typically leaves burrs on the walls of the stent which must be removed prior to use. The removal of these burrs is typically performed electrolytically (e.g. by electropolishing).

Hitherto, in order to remove such burrs, an electrode held on a jig has been inserted into one end of the stent and the stent has been immersed in an acid bath for electrode erosion of the burrs. Because of the fragility of the stent it is necessary that the electrode used should make contact with the interior of the stent, and electrodes used have hitherto taken the form of a bent wire or a pair of expanding tweezers which are inserted into the stent end. In an attempt to obtain a uniform treatment of the stent it has been necessary to remove it from the electrode during the course of any active treatment and to replace the stent so that the electrode is located at its other end. This is time consuming. Because stents are so fragile, they are apt to become damaged during this reversal process. Considerable skill is required in order to remove and replace the stents in this way. Furthermore, of course the fact that the electrodes are located at each of the two ends for approximately half of the processing operation will entail that the ends of the stent are processed in a different manner from of the remainder of its length.

Analogous problems arise if it is desired to electroplate a stent.

SUMMARY OF THE INVENTION

It is an object of the present invention to provide a new method for processing stents.

According to the present invention there is provided a method of processing stents in at least one liquid bath, wherein stents to be processed are placed on a jig comprising a plurality of wire electrodes, preferably in such manner that each electrode passes through and projects beyond the full length of a stent placed thereon, wherein stents carried by the jig are immersed in a liquid bath which contains an electrolyte and the stents are urged into contact with their associated electrodes while current is applied to those electrodes, and wherein positions of contact between the stents and their respective electrodes are altered during electrolysis without removing the stents from the jig.

The invention also includes a jig for supporting stents of pre-determined length (l) and internal diameter (d) during processing in a liquid medium which jig comprises an electrode support member holding a plurality of generally parallel wire electrodes each of which passes through a hole in a stent support bar, means for moving the stent support bar towards or away from the electrode support member in a direction along the electrodes, the wire electrodes having a diameter which is less than the predetermined stent internal diameter (d) and a length such that they can extend beyond the stent support bar by a distance which is greater that the predetermined stent length (l), and further comprising a plurality of contact positioning members selectively movable in relation to the electrodes for urging contact between each such electrode and a stent carried thereby.

Because the electrode runs the full length of the stent during processing any contact marking between the stents and the electrode will be more evenly distributed along the stent, and this is the more so because the positions of contact between the stents and their respective electrodes are altered during the processing. The stents remain supported by the electrodes throughout the electrolytic processing step. Accordingly no time is wasted in removing the stents from the bath and reversing them on the electrodes. This also avoids any risk of damage during such a reversing step. Risks of a local burning of the stent are substantially reduced by ensuring that the end of a the electrode projects through and beyond the full length of the stent.

Preferably, processing of the stents is performed in a succession of liquid baths while the stents are carried by the same jig, and in the most preferred embodiments of the invention, processing of the stents is performed in a succession of liquid baths, and all liquid-bath processing steps are performed while the stents are carried by the same jig. The adoption of one or both of these preferred features further reduces time which might be lost by reversing the stents on a jig and a consequent risk of damage to the stents. The requirement for skilled workers with a high degree of manual dexterity is also reduced. The processing steps may comprise pre-processing the stents prior to electropolishing or electroplating. For example, the stents may be cleaned as a pre-processing step (e.g. in an ultrasonic cleaning bath). The stents may be cleaned after electropolishing or electroplating.

While the present invention was made with particular reference to problems encountered in electro-polishing stents, it is equally applicable for use during an electroplating process. It is also applicable to other treatments of stents as part of the manufacturing process, such as cleaning steps, or surface treatment steps.

Preferably, the electrode support member, the stent support bar and the contact positioning members are formed of one or more non-conductive, acid-resistant material. The jig is thus suitable for use in electrolytic processes involving the use of an acidic electrolytic bath, as well as in other processes such as multi-stage rinsing processes. Individual control of the electrodes is enabled, and the contact positioning members will be least likely to have any effect on the process conducted.

Particularly suitable non-conductive, acid-resistant material(s) include high density polyethylene, polytetrafluoroethylene, polyvinylchloride, polyvinyldifluoride, polypropylene.

The electrodes are suitably formed of platinum wire.

Preferably, said stent support bar is movable between first and second positions and said contact positioning members are located at a distance of between l/3 and 2l/3 from the nearer of such positions, l being the predetermined stent length. This insures that the stent is urged against the electrode wire at a median position along its length, and this in turn promotes a greater contact area between the stent and the electrode. This further promotes uniform treatment of the stent.

In some preferred embodiments of the invention, means is provided for moving said contact positioning members to-and-fro in a direction generally parallel to the stent support bar. In this way contact will take place between the stent and the wire electrode at opposed positions on the inner wall of the stent.

In other preferred embodiments of the invention, said contact positioning members are annular and means is provided for moving them in an orbital manner about the wire electrodes. In that way contact positions between the electrode wire and the inner wall of the stent can be moved around the whole of the inner wall of the stent. Such contact position can be changed intermittently or continuously. This further promotes uniformity of treatment of the stent along its length.

Uniformity of contact between the inner wall of the stent and the wire electrode is further promoted when each said electrode is constituted by a smooth round wire, as is preferred.

The invention further extends to a stent processing plant incorporating a plurality of stent processing baths, at least one jig as herein defined, and means for transporting a said jig and immersing it in the successive processing baths.

DESCRIPTION OF THE DRAWINGS

A preferred embodiment of the invention will now be described with reference to the accompanying diagrammatic drawings of which:

FIG. 3 shows more structure of the jig of FIG. 2;

FIG. 4 shows schematically a stent electrolytic treatment closed system incorporating the jig of FIG. 2;

DESCRIPTION OF THE EMBODIMENT

Figure 1:
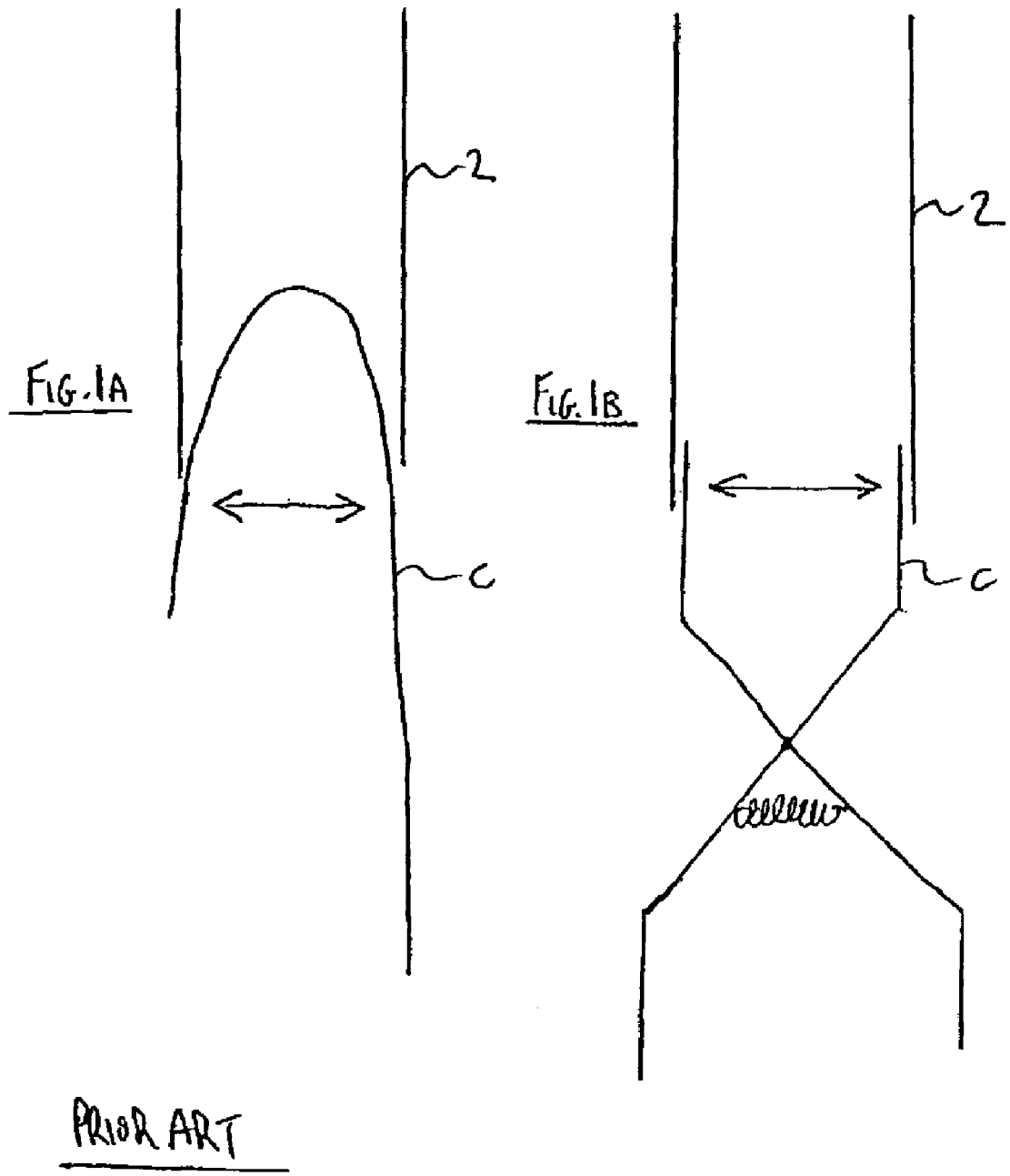
FIGS. 1A and 1B show prior art ways of holding stents for electropolishing.

FIGS. 1A and 1B show a stent, referenced 2, supported as in the prior art at one end only by a sprung clip C inserted into the end of the stent. In the case of FIG. 1A the clip is a bent piece of spring wire. In the case of FIG. 1B, it is a pair of tweezers that are spring-biased to open.

Figure 2:
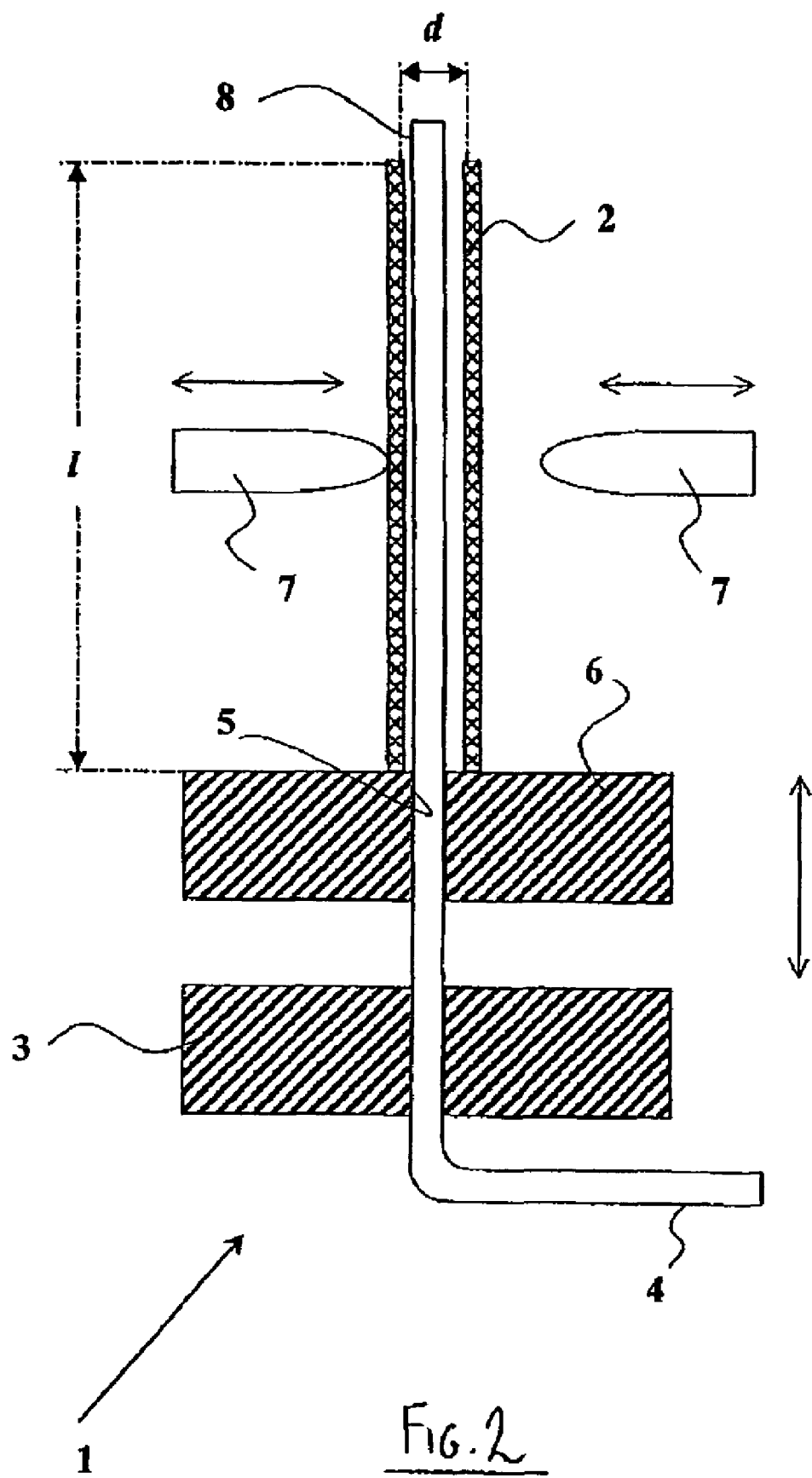
FIG. 2 shows a stent located on an electrode of a jig in accordance with one aspect of this invention.

In FIG. 2 is shown our new jig 1 for supporting stents 2 of a pre-determined length l and internal diameter d. The jig comprises an electrode support member 3 holding a plurality of first stent-engaging formations which in this embodiment are generally parallel wire electrodes 4 (or first members) each of which passes through a hole 5 in a stent support bar 6 of plastics, non-conducting, material. The wire electrode 4 has a diameter which is less than the internal diameter d of the stent and the stent is accordingly a loose fit on the electrode wire. A complementary set of a plurality of second stent-engaging formations, which in this embodiment are contact positioning members 7 (or second members), which are movable to and fro in a direction along the stent support bar 6, are arranged to urge one side of the inner wall of the stent, or the other, against the electrode 4. The members 7 are also made of non-conducting plastics material.

In operation, stents 2 are slipped over wire electrodes 4 and come to rest on the stent support bar 6. The stent support bar is raised or lowered so that a median portion of the stent 2 is aligned with the contact positioning members 7. The contact positioning members 7 may then be urged to one side or other so as to pin the stent against the electrode 4, whereupon the stent support bar 6 may be lowered out of contact with the stent so that it does not interfere with any treatment of the stent. The stent is pinned strongly enough to prevent it from sliding down, but not so strongly as to damage the wall of the stent.

Because the wire electrode 4 is long enough that its end 8 projects beyond the end of the stent, any irregularities or deformations of that end 8 of the wire electrode will not affect the processing carried out on the stent. In other embodiments, the wire 8 need not extend beyond the end of the stent; just into it.

Given a suitably precise construction and movement of the parts of the jig it is possible to insure that the stent will be in contact with the wire electrode 4 over substantially the whole length of the stent. This militates against any irregularity of treatment along the length of the stent. At a suitable stage during the processing the stent support bar 6 may be raised to contact the base of the stent 2, to support the stent, and the contact positioning members may be moved across to bring the other side of the stent into contact with the electrode. In an alternative arrangement the contact positioning members are moved across to pin a different part of the stent wall, without previously supporting the bottom of the stent. The stent may slide down the electrode 8, possibly to rest upon bar 6, whilst the pinning position is changed.

Movement of the various parts of the jig is suitably effected by one or more stepper motors, which may be controlled by a common microprocessor controller. A user may be able to select, or input, processing times or other control operations. A user-input interface (e.g. keyboard) may be provided.

Figure 6A:
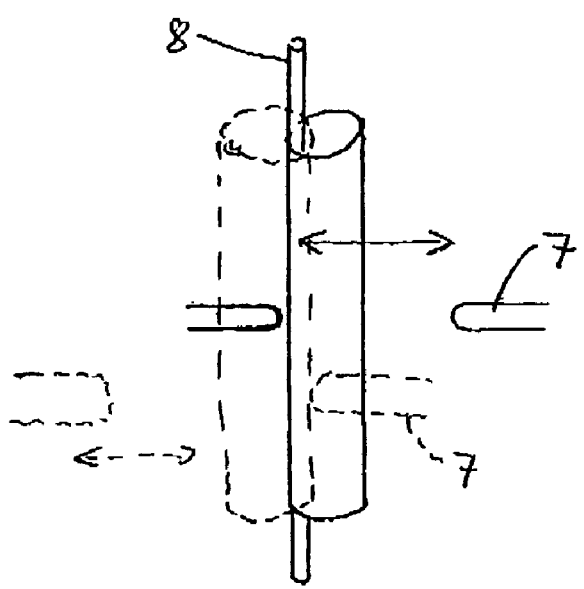
FIGS. 6A and 6B show alternative arrangements.
Figure 6B:
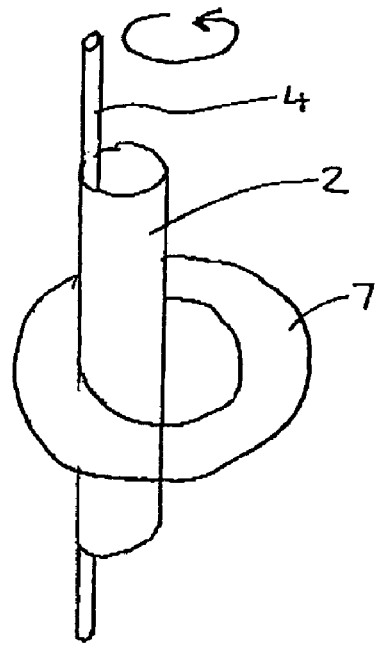

In a variant embodiment, shown in FIG. 6B, the contact positioning members 7 are each constituted by an annulus which is movable in an orbital manner, either stepwise or continuously, around the wire electrode 4 in order to vary the contact position between the stent 2 and the electrode 4 either stepwise or continually.

Adoption of the present invention in the electro polishing of stents primarily eliminates the need to turn the stent over. It may also give a reduced tendency of burning of the stent and may reduce any tendency to a differential polishing along the length of the stent. In particular, a stent manufactured using a jig in accordance with the invention can be substantially free from signs of non-uniform electrolytic contact at its ends.

Because stents do not require to be removed from the jig at any stage during the processing, it is relatively easy to construct a plant in which all the required processing baths are contained within a fume cupboard. This is plainly beneficial for the environment of those operating the plant. One or more of, or all of, reduced manufacturing times, labour costs, stent damage due to turning it over on its electrode, may also be achievable by embodiments of the invention.

FIG. 2 shows the ends of the contact positioning members 7 as being rounded and smooth. This helps prevent damaging the stent.

FIG. 3 shows a part of the jig 1. The jig may have about 20–30 tines of a comb-like structure 30, with each tine 31 comprising a strut 32 extending from a support bar 34, and having a contact positioning member 7 at the foot of the tine. A stepper motor 36 is shown to control the lateral position of the comb 30.

A stepper motor 38 is shown to control the height of the support bar 6 relative to the contact positioning member 7.

An optional stepper motor 40 is shown to control the height of the electrode support member 3 relative to the contact positioning members 7.

A microprocessor 42 controls the stepper motors.

FIG. 4 shows an enclosed cabinet 44 (schematically represented by chain dotted line 46) which has atmosphere control for the processes that occur inside it. The cabinet 44 has a stent treatment line inside it, including a jig 1 in accordance with the invention. The treatment line has a first pre-treatment liquid bath 50, a cleaning bath 52, an electropolishing bath 54, and a second cleaning bath 56.

The jig 1 is supported by, and driven on, rails 58 and can move from bath to bath, and the jig can be raised and lowered into each bath.

Figure 7:
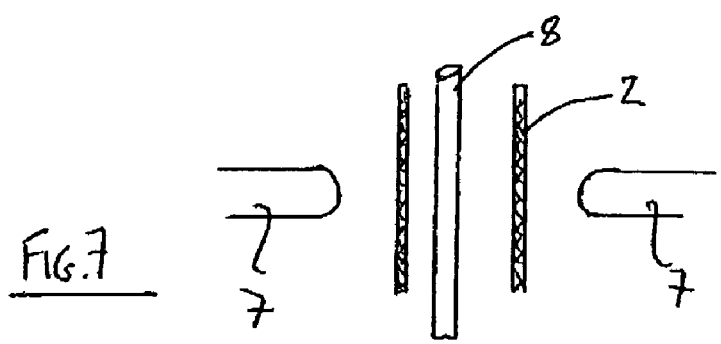
FIG. 7 shows another feature of the embodiment of FIG. 2.

The contact positioning members 7 can be set to a third, neutral, position relative to the electrode 8, in which no force is applied to the side wall of the stent. Indeed, the side walls of the stent may not touch the contact positioning members: the stent is "loose" on the first member. This is shown in FIG. 7. As can be seen there is space, or can be space, between the inner walls of the stent and the electrode. In this "non-biased" position liquid in a liquid bath can contact all curved surfaces of the stent. This can be useful in a cleaning, or other pre-treatment, operation where good electrical contact with the stent is not necessary. Indeed, we have a machine and process in which the same jig is used to carry the stents for pre-treatment steps as is used during electropolishing (or electroplating). This removes the need to transfer stents from one jig to another (as is done in the prior art). This may constitute a separate inventive step, and protection for that concept is sought.

FIG. 6A shows an arrangement where it is the contact support member 7 that moves and pushes the stent into the opposite side of the electrode 8, with the electrode being stationary.

Figure 5A:
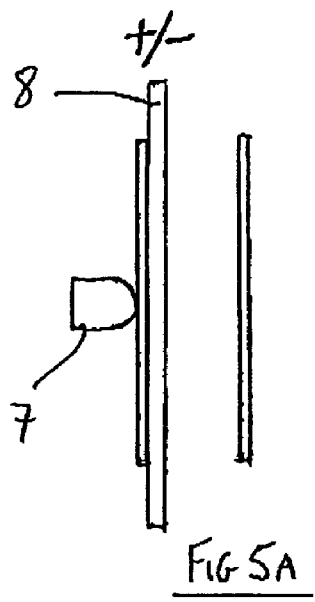
FIGS. 5A and 5B show alternative arrangements of the jig of FIG. 2.
Figure 5B:
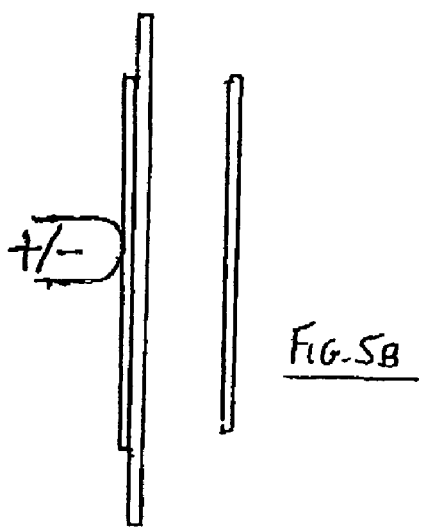

FIG. 5A shows an arrangement where the first member 8 is an electrode and the contact support member is non-conductive. FIG. 5B shows the opposite: the contact support member, or second member, is an electrode (shown by "+/−"), and the first member, inside the stent, is non-conductive. Alternatively the first member and the second member may be conductive. It is preferred to have the arrangement of FIG. 5A.

The contact support member 7 may itself have a substantial elongate extent, and may comprise a wire or rod. The stent may be held between two wires/rods extending parallel to each other.

Figure 8A:
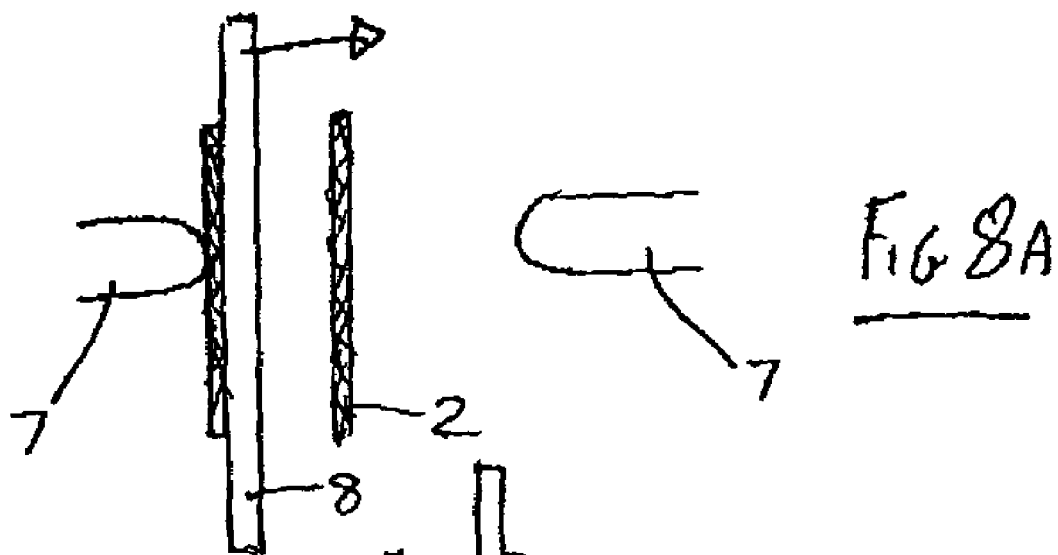
FIG. 8 shows a modification.
Figure 8B:
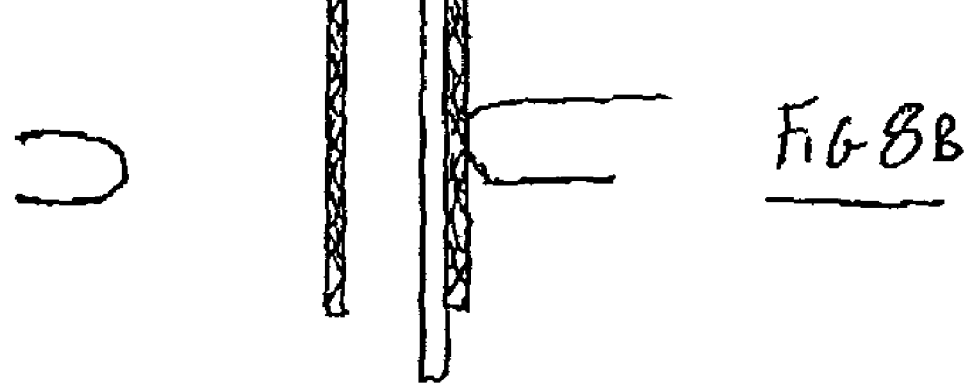
Figure 8C:
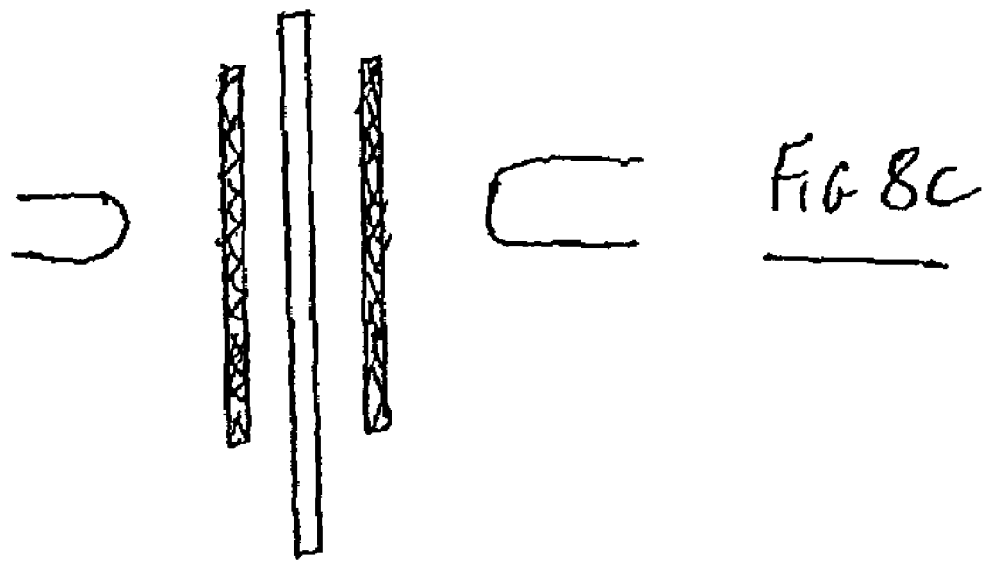

FIGS. 8A to 8C show an arrangement where it is the electrode, or first member 8, that moves, and the contact support member 7 that remains stationary. Of course, both the contact support member and first member may move.

Stents come in different diameters and lengths. For example, 0.5 mm diameter to 2 mm diameter, and from 5 mm to 40 mm in length. The precise dimensions are not important to the point being made now. The same jig, with the same first and second members, is suitable for a wide variety of lengths and diameters of stents. This is not true of the prior art, where the strength of the spring force applied to the stent was chosen to suit a stent of a specific diameter. Reacting the pinning force directly through the wall helps in this regard.

Although we have shown the same first member contacting two different parts of the inner stent wall at different times, we could of course use two different first members: one for each position of contact. Protection for this is sought, and "first member" should be read so as to include different members at different times.

What is claimed is:

1. A liquid bath treatment jig adapted to treat stents, the jig comprising:
   a set of a plurality of first stent-engaging formations adapted to be inserted inside respective stents;
   a complementary set of a plurality of second stent-engaging formations adapted to engage an outside wall of respective stents;
   wherein one of the first and second stent-engaging formations is conductive and the other is non-conductive;
   pairs of first and second formations being adapted to hold a stent between them at a first position on the stent, when the formations are in a first position relative to each other;
   pairs of the first and second formations being adapted to hold a stent at a different, second, position on the stent so as to expose said first position on the stent, in use, to liquid of the bath, when the formations are in a second, different, position relative to each other; and
   in which movement of the sets of first stent-engaging formations relative to the second set of stent-engaging formations is in a plane that is generally normal to an elongate direction of the first stent-engaging formations and adapted to occur without removing the stents from the first formations.

2. A jig according to claim 1 in which the first and second sets of formations are adapted to move in a straight line relative to each other between the first and second relative positions.

3. A jig according to claim 1 in which a stent support is adapted to support the stents in place whilst relative movement between the first and second formations occurs.

4. A jig according to claim 1 in which the stents are adapted to be moved laterally relative to the first formations which extend into them in use.

5. A jig according to claim 1 in which a comb of second formations is carried by a carrier and is adapted to be moved relative to an array of first formations so as to move said second formations simultaneously.

6. A jig according to claim 1 in which an array of first formations are adapted to be moved simultaneously relative to said second formations.

* * * * *